(12) United States Patent
Major et al.

(10) Patent No.: US 8,865,941 B2
(45) Date of Patent: Oct. 21, 2014

(54) PROCESS FOR THE PREPARATION OF ALKYLDIAMINES

(75) Inventors: Michael D. Major, Evanston, IL (US); David W. Moore, Hebron, IL (US)

(73) Assignee: ANGUS Chemical Company

(*) Notice: Subject to any disclaimer, the term of this patent is extended or adjusted under 35 U.S.C. 154(b) by 0 days.

(21) Appl. No.: 14/117,429

(22) PCT Filed: May 17, 2012

(86) PCT No.: PCT/US2012/038336
§ 371 (c)(1),
(2), (4) Date: Nov. 13, 2013

(87) PCT Pub. No.: WO2012/173735
PCT Pub. Date: Dec. 20, 2012

(65) Prior Publication Data
US 2014/0200371 A1    Jul. 17, 2014

Related U.S. Application Data

(60) Provisional application No. 61/496,135, filed on Jun. 13, 2011.

(51) Int. Cl.
C07C 209/34 (2006.01)
C07C 211/11 (2006.01)

(52) U.S. Cl.
CPC .................................. *C07C 209/34* (2013.01)
USPC .......................................... 564/494; 564/511

(58) Field of Classification Search
CPC ...................................................... C07C 209/34
USPC .................................................. 564/494, 495
See application file for complete search history.

(56) References Cited

U.S. PATENT DOCUMENTS

| 2,408,171 | A |   | 9/1946  | Johnson |         |
|-----------|---|---|---------|---------|---------|
| 2,408,172 | A | * | 9/1946  | Johnson | 564/473 |
| 2,413,248 | A |   | 12/1946 | Senkus  |         |
| 3,564,057 | A | * | 2/1971  | Tindall | 564/495 |
| 3,594,419 | A | * | 7/1971  | Rosenthal | 564/494 |
| 6,888,030 | B2 | * | 5/2005 | Su et al. | 564/494 |
| 2011/0224460 | A1 | * | 9/2011 | Moore | 564/494 |

FOREIGN PATENT DOCUMENTS

| JP | 2005 298495 A | 10/2005 |
|----|---------------|---------|
| WO | 2005/113512 A1 | 12/2005 |

OTHER PUBLICATIONS

Jones, et al., "Reactions of Nitroparaffins. Part II. The Reaction of 2-Nitropropane with Formaldehyde and Ammonia", J. Chem Soc., pp. 1766-1767 (1949).

* cited by examiner

*Primary Examiner* — Brian J Davis
(74) *Attorney, Agent, or Firm* — Raef M. Shaltout

(57) ABSTRACT

Provided is a process for preparing alkyl diamine compounds in high purity. The process utilizes an alkyl amine compound during the reduction of a nitroamine, resulting in reduction of the concentration of undesired byproducts.

11 Claims, No Drawings

PROCESS FOR THE PREPARATION OF ALKYLDIAMINES

CROSS-REFERENCE TO RELATED APPLICATIONS

This application is a 35 USC §371 national phase of PCT/US2012/038336 filed May 17, 2012, which claims priority from provisional application Ser. No. 61/496,135, filed Jun. 13, 2011, which is incorporated herein by reference in its entirety.

BACKGROUND

This invention relates generally to a process for preparing high purity alkyl diamines compounds.

Alkyl diamines are compounds that find use as intermediates in the synthesis of many end-use products, such as pharmaceuticals, dyes, cosmetics, and agricultural materials. Because many of these products are used, or even consumed, by humans, manufacturers of such products require that the alkyl diamine be of high purity. Known processes for making alkyl diamines, however, either do not provide the desired level of purity, or else are too cumbersome or elaborate to be cost effective on a commercial scale.

For instance, 2-methyl-1,2-diaminopropane (MDP) is a pharmaceutical intermediate that has a very stringent purity requirement. Typical processes for producing high-purity material are often very expensive due to the use of unique and costly reagents and are often not amenable to production in industrial facilities. Certain impurities are of particular concern to manufacturers of end-use pharmaceuticals. Of particular concern is the presence of a secondary-amine impurity conventionally formed during the reduction step (N-methyl-MDP) since this impurity is very difficult to remove by ordinary distillation processes.

The problem addressed by this invention is the provision of a commercially viable process for preparing high-purity alkyl diamines, such as MDP.

STATEMENT OF INVENTION

We have now found that when making alkyl diamines via the reduction of a nitroamine, conducting the reduction in the presence of an alkylamine compound yields a product having increased purity. Advantageously, the process is simple and commercially viable, and alkyl diamine compounds for use in applications with stringent purity requirements may now be readily prepared.

Accordingly, in one aspect, there is provided a process for preparing a diamine compound of formula I:

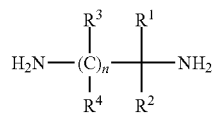

wherein n is an integer from 1 to 5; $R^1$ and $R^2$ are independently H or $C_1$-$C_6$ alkyl, or $R^1$ and $R^2$ together with the carbon to which they are attached form $C_3$-$C_{12}$ cycloalkyl; and $R^3$ and $R^4$ at each occurrence are independently H or $C_1$-$C_6$ alkyl, the process comprising reducing a corresponding nitroamine compound, wherein the reduction is conducted in the presence of an alkylamine compound of formula II:

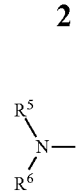

wherein $R^5$ is H or $C_1$-$C_6$ alkyl and $R^6$ is $C_1$-$C_6$ alkyl.

In another aspect, there is provided a process for preparing 2-methyl-1,2-diaminopropane, the process comprising: hydrogenating 2-nitro-2-methyl-1-propylamine in the presence of hydrogen gas, a hydrogenation catalyst, and n-propylamine.

In a further aspect there is provided a composition comprising 2-methyl-1,2-diaminopropane and less than 0.6 weight percent of its N-methylated derivative.

DETAILED DESCRIPTION

Unless otherwise indicated, numeric ranges, for instance as in "from 2 to 10," are inclusive of the numbers defining the range (e.g., 2 and 10).

Unless otherwise indicated, ratios, percentages, parts, and the like are by weight.

"Alkyl," as used in this specification encompasses straight and branched chain aliphatic groups having the indicated number of carbon atoms. If no number is indicated (e.g., aryl-alkyl-), then 1-6 alkyl carbons are contemplated. Examples of alkyl groups include, without limitation, methyl, ethyl, propyl, isopropyl, butyl, isobutyl, sec-butyl, tert-butyl, pentyl, and hexyl. Unless otherwise indicated, the alkyl group is optionally substituted with 1, 2, or 3, preferably 1 or 2, more preferably 1, substituents that are compatible with the syntheses described herein. Such substituents include, but are not limited to, nitro, halogen, carboxylic acids (e.g., $C_0$-$C_6$—COOH), and $C_2$-$C_6$ alkene. Unless otherwise indicated, the foregoing substituent groups are not themselves further substituted. In some embodiments, alkyl is unsubstituted.

The term "cycloalkyl" refers to saturated and partially unsaturated cyclic hydrocarbon groups having the indicated number of ring carbon atoms. If no number is specified, then 3 to 12 carbons, preferably 3 to 8 carbons, and more preferably 3 to 7 carbons, are contemplated. Preferred cycloalkyl groups include, without limitation, cyclopropyl, cyclobutyl, cyclopentyl, cyclopentenyl, cyclohexyl, cyclohexenyl, cycloheptyl, and cyclooctyl. Unless otherwise indicated, the cycloalkyl group is optionally substituted with 1, 2, or 3, preferably 1 or 2, more preferably 1, substituents that are compatible with the syntheses described herein. Such substituents include, but are not limited to, $C_1$-$C_6$ alkyl, nitro, halogen, carboxylic acids (e.g., $C_0$-$C_6$—COOH), and $C_2$-$C_6$ alkene. A preferred substituent is $C_1$-$C_6$ alkyl. In some embodiments, cycloalkyl is unsubstituted or is substituted only with $C_1$-$C_6$ alkyl.

In the invention, alkyl diamine compounds of formula I are prepared by reduction of a nitroamine compound. The reduction is carried out in the presence of an alkylamine compound. The nitroamine compound that is subjected to reduction is a mono-nitro mono-amine with a structure that corresponds to the desired alkyl diamine. Thus, the nitroamine may be represented by the following formula:

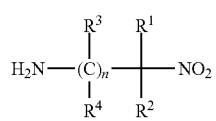

wherein n is an integer from 1 to 5; $R^1$ and $R^2$ are independently H or $C_1$-$C_6$ alkyl, or $R^1$ and $R^2$ together with the carbon to which they are attached form $C_3$-$C_{12}$ cycloalkyl; and $R^3$ and $R^4$ at each occurrence are independently H or $C_1$-$C_6$ alkyl. Nitroamine compounds of the foregoing formula may be commercially available or they may be readily prepared by those skilled in the art. For instance, nitroamine compounds may be prepared by the reaction of formaldehyde, ammonia, and a nitroalkane/cycloalkane compound. Exemplary syntheses are described in *J. K. N. Jones and T. Urbanski*, "Reactions of Nitroparaffins. Part II. The Reaction of 2-Nitropropane with Formaldehyde and Ammonia", J. Chem Soc. 1766 (1949), and in U.S. Pat. No. 2,408,171 which is incorporated herein by reference.

As noted, in the invention, the reduction of the nitroamine is conducted in the presence of an alkyl amine compound. The alkyl amine compound may be represented by the following formula II:

wherein $R^5$ is H or $C_1$-$C_6$ alkyl and $R^6$ is $C_1$-$C_6$ alkyl. In some embodiments of the invention, $R^5$ is H. In some embodiments, $R^5$ is H and $R^6$ is methyl, ethyl, n-propyl, isopropyl, butyl, isobutyl, sec-butyl, tert-butyl, pentyl, or hexyl. In some embodiments, the alkyl amine compound is n-propylamine. Alkyl amine compounds of formula II are commercially available or they may be readily prepared by those skilled in the art.

The amount of alkyl amine compound of formula II may range from 1 to 10 mole percent based on the quantity of the nitroamine compound. In some embodiments, the amount is from 1 to 3 mole percent.

The reduction of the nitroamine compound to the alkyl diamine, in the presence of the alkylamine, may be carried out using any reagent capable of reducing aliphatic nitro groups. Examples of such reducing agents include hydrogen gas in combination with a hydrogenation catalyst, for example, Raney nickel or a cobalt, platinum or palladium based catalyst (Co, Pt or Pd in elemental form or as oxides, with or without supports, e.g., carbon); and other reducing agents including metal/acid combinations, e.g., iron/acetic acid; or aluminum hydrides, e.g., VITRIDE. Preferred reducing agents include hydrogen gas in combination with any of the following catalysts: Raney nickel, platinum, or palladium. Conditions for hydrogenation of nitro groups are well known, e.g., a temperature range of about 30° C. to 100° C. at a pressure of about 700 kPa to 7000 kPa are typical, although these can be readily adjusted by one skilled in the art. In some embodiments, lower pressures and/or temperatures are preferred. For instance, in some embodiments, the pressure may be from 4100-4240 kPa. In some embodiments, the temperature may be from 35 to 55° C., alternatively from 40 to 50° C.

By way of specific example of a typical procedure utilizing hydrogen and a hydrogenation catalyst, the alkyl amine and hydrogenation catalyst are charged to a high pressure reactor, such as a Parr autoclave. A solvent, such as methanol, may also be added. The reactor is sealed and pressurized with hydrogen gas. The nitroamine compound, which may be in the form of a solution such as an aqueous solution, is charged to the reactor and the temperature of the reactor increased to the desired level. Following sufficient time for the reaction to occur, the temperature and pressure may be reduced and the product mixture removed from the reactor. The alkyl diamine compound may be isolated by techniques well known in the art, such as distillation.

The alkyl diamine formed by the process of the invention is a compound of formula I:

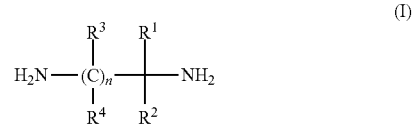

wherein n is an integer from 1 to 5; $R^1$ and $R^2$ are independently H or $C_1$-$C_6$ alkyl, or $R^1$ and $R^2$ together with the carbon to which they are attached form $C_3$-$C_{12}$ cycloalkyl; and $R^3$ and $R^4$ at each occurrence are independently H or $C_1$-$C_6$ alkyl.

In some embodiments, n in the alkyl diamine of formula I (and its corresponding nitroamine) is 1-4, alternatively 1-3, alternatively 1-2 or alternatively it is 1.

In some embodiments, $R^1$ and $R^2$ in the alkyl diamine of formula I (and its corresponding nitroamine) are independently $C_1$-$C_6$ alkyl, alternatively they are independently $C_1$-$C_4$ alkyl, or alternatively independently $C_1$-$C_2$ alkyl. In some embodiments, both $R^1$ and $R^2$ are methyl.

In some embodiments, $R^1$ and $R^2$ in the alkyl diamine of formula I (and its corresponding nitroamine), together with the carbon to which they are attached, form $C_3$-$C_{12}$ cycloalkyl, alternatively $C_4$-$C_7$ cycloalkyl, or alternatively $C_5$-$C_6$ cycloalkyl. In some embodiments, $R^1$ and $R^2$ together with the carbon to which they are attached form cyclopentyl or cyclohexyl.

In some embodiments, $R^3$ and $R^4$ in the alkyl diamine of formula I (and its corresponding nitroamine) at each occurrence are independently H or $C_1$-$C_4$ alkyl, alternatively H or $C_1$-$C_2$ alkyl. In some embodiments, they are H at all occurrences.

In some embodiments, the alkyl diamine compound of formula I is 2-methyl-1,2-diaminopropane (and the corresponding nitroamine compound is 2-nitro-2-methyl-1-propylamine), 1-amino-cyclopentanemethanamine, 1-amino-cyclohexanemethanamine, or 2-amino-2-methyl-1-aminobutane.

The process of the invention provides alkyl diamine compounds of formula I in high purity. In particular, inclusion of the alkyl amine compound of formula II in the process provides product that contains reduced amounts of an N-alkylated derivative by-product of the formula I dialkyl amine, which is typically difficult to remove from the desired product. In contrast, the alkyl amine or its N-alkylated derivative is much easier to remove.

By "high purity" is meant that the product from the inventive process, prior to undergoing purification steps such as distillation, contains less than 5, alternatively less than 3, alternatively less than 1, alternatively less than 0.6, or alternatively less than 0.3 weight percent of N-alkylated derivative (of the alkyl diamine) based on the weight of the alkyl diamine compound. The amount may be readily determined for instance by gas chromatography. In some embodiments, the product is free of the N-alkylated derivative of the alkyl diamine (as measured by gas chromatography).

In a preferred embodiment, the invention provides 2-methyl-1,2-diaminopropane (MDP) containing less than 0.6, alternatively less than 0.3 weight percent of N-alkylated derivatives such as N-methyl MDP ($N^1$,2-dimethylpropane-1,2-diamine). In some embodiments, the invention provides MDP that is free of N-alkylated derivatives such as N-methyl MDP.

Alkyl diamine compounds prepared as described herein find use in a variety of applications, including for instance as intermediates in the synthesis of pharmaceutical compounds.

Some embodiments of the invention will now be described in detail in the following Examples.

EXAMPLES

Example 1

High Purity 2-methyl-1,2-diaminopropane

2-Nitro-2-methyl-1-propylamine. The 2-nitro-2-methyl-1-propylamine may be produced by any convenient means, such as the one described by H. G. Johnson in U.S. Pat. No. 2,408,171. For example 238 grams of 2-methyl-2-nitro-1-propanol is added to a steel vessel which is then cooled to a temperature near −35° C. by any means, such as cooling with solid carbon dioxide. When the desired temperature is reached, 340 grams of liquid ammonia is added and the vessel is sealed. Then the reaction vessel is heated to a temperature of about 40 to about 80° C., preferably about 65° C. until the reaction is complete: about two hours, depending on the temperature. The ammonia is then vented from the reaction vessel and the aqueous solution of 2-nitro-2-methyl-1-propylamine is left in the vessel appearing as a yellow liquid.

2-Methyl-1,2-diaminopropane. A 300 ml Parr autoclave is charged with 45.2 grams of methanol, 1.9 grams of n-propylamine, and 3.1 grams of Grace Raney Nickel. The reactor is sealed and pressurized to 4080 kPa with pure hydrogen and agitated at 600 rpm. A solution of 2-nitro-2-methyl-1-propylamine in water (prepared as described above) is then pumped to the pressurized reactor at a rate of about 0.8 g/min. The reactor temperature is allowed to rise from ambient to 52° C. and is controlled by the Parr controller at a temperature between 49 and 52° C. The hydrogen pressure is controlled via an on demand regulator and was maintained between 3944 kPa and 4185 kPA through the duration of the reaction. When the feed is complete, a charge of 21.6 grams of methanol is fed through the pump used to clear the lines of residual nitroamine. This material is also charged to the reactor. When the methanol charge is completed, the mixture is held at 52° C., 4110 kPa for 20 minutes and then the agitation stopped.

A sample is removed from the reaction and analyzed by gas chromatograph (GC). GC shows no methyl impurity. BY GC, the MDP is 79.5% pure with 0.0% N-methyl-MDP. Correcting for the propylamine, which shows up as an impurity, the MDP is 87.3% pure.

Example 2 (Comparative)

2-methyl-1,2-diaminopropane by Conventional Process

Example 1 is repeated using substantially the same conditions except that no N-propylamine is added to the reactor. GC indicates that the product MDP is 84.4% pure but contains 0.6% N-methyl-MDP.

Example 3 (Prophetic)

High Purity 1-Amino-cyclopentanemethanamine

High purity 1-amino-cyclopentanemethanamine may be prepared using essentially the same procedures as described in Example 1 except for substituting nitrocyclopentane as the starting nitroalkane and making non-critical modifications as needed.

Example 4 (Prophetic)

High Purity 1-Amino-cyclohexanemethanamine

High purity 1-amino-cyclohexanemethanamine may be prepared using essentially the same procedures as described in Example 1 except for substituting nitrocyclohexane as the starting nitroalkane and making non-critical modifications as needed.

Example 5 (Prophetic)

High Purity 2-Amino-2-methyl-1-aminobutane

High purity 2-amino-2-methyl-1-aminobutane may be prepared using essentially the same procedures as described in Example 1 except for substituting 2-nitrobutane as the starting nitroalkane and making non-critical modifications as needed.

What is claimed is:

1. A process for preparing an alkyl diamine compound of formula I:

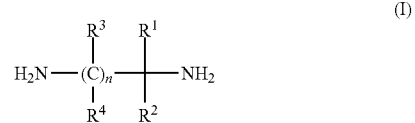

wherein n is an integer from 1 to 5; $R^1$ and $R^2$ are independently H or $C_1$-$C_6$ alkyl, or $R^1$ and $R^2$ together with the carbon to which they are attached form $C_3$-$C_{12}$ cycloalkyl; and $R^3$ and $R^4$ at each occurrence are independently H or $C_1$-$C_6$ alkyl, the process comprising reducing a corresponding nitroamine compound, wherein the reduction is conducted in the presence of an alkylamine compound of formula II:

wherein $R^5$ is H or $C_1$-$C_6$ alkyl and $R^6$ is $C_1$-$C_6$ alkyl.

2. The process of claim 1 wherein n is 1.
3. The process of claim 1 wherein $R^3$ and $R^4$ are H.
4. The process of claim 1 wherein $R^1$ and $R^2$ are independently $C_1$-$C_3$ alkyl.
5. The process of claim 1 wherein $R^1$ and $R^2$ together with the carbon to which they are attached form $C_5$-$C_6$ cycloalkyl.
6. The process of claim 1 wherein the alkyl diamine compound of formula I is 2-methyl-1,2-diaminopropane, 1-amino-cyclopentanemethanamine, 1-amino-cyclohexanemethanamine, or 2-amino-2-methyl-1-aminobutane.

7. The process of claim 1 wherein $R^5$ is H and $R^6$ is $C_1$-$C_6$ alkyl.

8. The process of claim 1 wherein the alkylamine compound of formula II is n-propylamine.

9. The process of claim 1 wherein the reduction is carried out with hydrogen gas in combination with a hydrogenation catalyst.

10. A process for preparing 2-methyl-1,2-diaminopropane, the process comprising: hydrogenating 2-nitro-2-methyl-l-propylamine in the presence of hydrogen gas, a hydrogenation catalyst, and n-propylamine.

11. A composition comprising 2-methyl-1,2-diaminopropane and less than 0.6 weight percent of its N-methylated derivative prior to distillation, wherein the composition is prepared by the process of claim 10.

* * * * *